United States Patent [19]
Zhou et al.

[11] Patent Number: 5,444,106
[45] Date of Patent: Aug. 22, 1995

[54] HIGH REFRACTIVE INDEX SILICONE COMPOSITIONS

[75] Inventors: Stephen Q. Zhou, Hacienda Heights; Jennifer C. Sy; Michelle A. Berteig, both of Monrovia, all of Calif.; Thomas P. Richards, Shelton, Wash.

[73] Assignee: Kabi Pharmacia Ophthalmics, Inc., Monrovia, Calif.

[21] Appl. No.: 173,187

[22] Filed: Dec. 23, 1993

Related U.S. Application Data

[63] Continuation-in-part of Ser. No. 871,335, Apr. 21, 1992, abandoned.

[51] Int. Cl.$^6$ .................................................. C08K 3/36
[52] U.S. Cl. ...................................... 523/107; 525/478; 525/479; 528/15; 528/31; 528/32; 524/862; 523/105
[58] Field of Search ............... 525/478, 479; 528/15, 528/31, 32; 524/862; 523/107, 105

[56] References Cited

U.S. PATENT DOCUMENTS

| | | | |
|---|---|---|---|
| 3,635,743 | 1/1972 | Smith | 106/288 Q |
| 3,996,189 | 12/1976 | Travnicek | 260/37 SB |
| 4,198,131 | 4/1980 | Birdsall et al. | 351/160 R |
| 4,470,668 | 9/1984 | Inoue et al. | 350/343 |
| 4,528,314 | 7/1985 | Modic | 534/407 |
| 4,753,978 | 6/1988 | Jensen | 524/862 |
| 4,868,251 | 9/1989 | Reich et al. | 525/479 |
| 4,882,398 | 11/1989 | Mbah | 525/478 |
| 4,929,669 | 5/1990 | Jensen | 524/861 |
| 4,946,893 | 8/1990 | Saito et al. | 524/862 |
| 4,985,525 | 1/1991 | Clark et al. | 528/15 |
| 5,023,288 | 6/1991 | Hirai et al. | 524/268 |
| 5,082,886 | 1/1992 | Jeram et al. | 524/403 |
| 5,133,746 | 7/1992 | Brady et al. | 623/6 |
| 5,147,394 | 9/1992 | Siepser et al. | 623/6 |
| 5,147,396 | 9/1992 | Kageyama et al. | 623/6 |
| 5,201,763 | 4/1993 | Brady et al. | 623/6 |

FOREIGN PATENT DOCUMENTS

| | | | |
|---|---|---|---|
| 0293560 | 12/1988 | European Pat. Off. | C08L 83/04 |
| 2309599 | 4/1975 | France . | |
| 2041633 | 3/1971 | Germany . | |
| 54-34362 | 3/1979 | Japan . | |
| 61-157569 | 7/1986 | Japan | C08K 13/02 |

*Primary Examiner*—John C. Bleutge
*Assistant Examiner*—Margaret W. Glass
*Attorney, Agent, or Firm*—Poms, Smith, Lande & Rose

[57] ABSTRACT

Organosiloxane compositions curable to optically clear, high refractive index elastomers are disclosed. The cured compositions have superior post-folding high resolution recovery making them suitable for fabricating foldable intraocular lenses used in small-incision ophthalmic surgeries. The organosiloxane compositions include first and second vinyl terminated organosiloxanes differing in molecular weights, each containing diphenylsiloxane and dimethylsiloxane, and, in addition, fumed silica, a crosslinking reagent, a platinum containing catalyst, and optionally an ultraviolet absorbing compound.

22 Claims, No Drawings

HIGH REFRACTIVE INDEX SILICONE COMPOSITIONS

This is a continuation in part of application Ser. No. 07/871,335, filed Apr. 21, 1992, now abandoned.

BACKGROUND OF THE INVENTION

1. Field of the Invention

The present invention is generally related to curable silicone compositions. More particularly, the present invention is related to organosiloxane copolymer compositions which cure to an elastomer having superior optical resolution, excellent folding recovery and high refractive indices, making them particularly suitable for fabricating foldable intraocular lenses.

2. Description of Related Art

Silicones are used extensively for applications in which optical quality materials having resilient characteristics are preferred. A particularly suitable application for optically clear silicone elastomers is in the fabrication of lenses which are surgically implanted in the eye as a replacement for the natural lens. Known as intraocular lenses, these are most frequently implanted subsequent to cataract surgery which results in the extraction of the natural lens. Advantageously, silicone is a suitably inert material and is well tolerated in the eye. Moreover, when carefully formulated, silicone based compositions can be prepared which have suitable mechanical strengths and sufficiently high optical resolution for use as a human prosthetic lens.

Intraocular lens implant procedures involve preparing an incision in the eye, passing the lens into the eye, and then suitably anchoring the lens within the eye so that it does not subsequently become dislodged. Procedures in which non-resilient lenses are implanted, for example, polymethylmethacrylate intraocular lenses, require incisions which are at least as long as the lens diameter or 6–8 mm. During the past decade small incision surgery has become increasingly popular among ophthalmic surgeons. These techniques involve implanting foldable intraocular lenses through incisions as little as 2 mm. Because silicone elastomer intraocular lenses can be folded or rolled into configurations having a reduced cross-sectional diameter, these types of lenses have grown in popularity.

Foldable intraocular lenses are preferably as thin as possible to provide reduced folded cross-sectional areas. Thinner lenses are also much easier to fold or roll into a configuration which is easily inserted. A problem associated with silicone based intraocular lenses is the inherently low refractive index of the most common and strongest polyorganosiloxane, polydimethylsiloxane ($n_D = 1.40$). As a result, lenses prepared from such materials having a low refractive index are thicker than lenses having the same degree of sight correction prepared from a higher refractive index material. Accordingly, optically effective polydimethylsiloxane based intraocular lenses are typically too thick for conveniently folding or rolling into shapes having minimum cross-sectional area.

In order to fabricate thinner foldable silicone intraocular lenses some lens manufacturers have provided silicone compositions with increased refractive indices. For example, a higher refractive index silicone has been prepared by replacing at least part of the dimethylsiloxane with the much weaker diphenylsiloxane which has a much higher refractive index. However, in order for the polyorganosiloxanes of dimethylsiloxane and diphenylsiloxane to provide optically clear cured elastomers, the crosslinking reagent and filler must match the refractive index of the polyorganosiloxane.

Typical organosiloxane crosslinking reagents, such as copolymers of methylhydrosiloxane and dimethylsiloxane, have low refractive indices. When these copolymers are utilized in the cure of diphenylsiloxane copolymers, the final cured elastomer is found to be hazy or even opaque. Similar problems are raised if the refractive index of any filler used is not matched to the refractive index of the polyorganosiloxane.

Furthermore, there are other major problems associated with intraocular lenses prepared from these elastomers, including poor optical resolution and the inability for these lenses to recover sufficient optical resolution once they are unfolded from a folded configuration. Optical clarity associated with a particular material does not necessarily guarantee good optical resolution and folding recovery.

Additionally, silicone based intraocular lenses are typically prepared with silicone based polyorganosiloxanes having a significant amount of low molecular weight material. The presence of the low molecular weight silicones can be responsible for significant lens shrinkage and weight loss.

Accordingly, it is an objective of the present invention to provide a curable optically clear silicone composition having a high refractive index.

It is also an objective of the present invention to provide a curable silicone composition useful for fabricating intraocular lenses having a low folded profile.

It is further an objective of the present invention to provide a curable silicone composition useful for fabricating intraocular lenses having superior optical resolution and folding recovery.

SUMMARY OF THE INVENTION

The present invention accomplishes the above-identified objectives and others by providing curable polyorganosiloxane compositions which vulcanize to optically clear silicone elastomers having refractive indices of at least 1.46. Since the curable polyorganosiloxane compositions of the present invention additionally demonstrate superior optical resolution characteristics and near 100% post-folding optical resolution recovery, they are particularly suitable for fabricating foldable intraocular lenses used in small incision intraocular lens implant surgery.

More particularly, the present invention provides high refractive index, curable polyorganosiloxane compositions which include at least two vinyl terminated polyorganosiloxane copolymers, a crosslinking agent, and a filler. Each of the two vinyl terminated polyorganosiloxane copolymers contains from about 80 mole % to about 95 mole % dimethylsiloxane and from about 5 mole % to about 20 mole % diphenylsiloxane.

The first vinyl terminated polyorganosiloxane is present at a concentration of from about 30% to about 55% and has a molecular weight range sufficient to provide a first vinyl terminated polyorganosiloxane copolymer viscosity of from about 400 cps to about 2500 cps. The second vinyl terminated polyorganosiloxane is present at a concentration of from about 45% to about 70% and has a molecular weight range sufficient to provide a second vinyl terminated polyorganosiloxane copolymer viscosity of from about 2500 cps to about 9500 cps.

Additionally, the polyoganosiloxane compositions of the present invention include at least one organohydrosiloxane crosslinking reagent. For example, a multifunctional organohydropolysiloxane crosslinking reagent, such as tetrakis(dimethylsiloxy)silane, which has a $SiO_2$ structure unit for the central silicon atom, contributes to the optical clarity of the composition and to the improved strength in the resulting cured elastomer. Exemplary embodiments also include a filler material and may include a catalyst and inhibitor as known in the art. In order to assure a high level of optical clarity, filler material in preferred exemplary embodiments is small particle sized fumed silica. Particularly preferred is fumed silica having the smallest particle size commercially available. An average particle size of about 7 nm and a refractive index, $n_D$ of 1.46 have proved to be particularly effective. Even more preferred is fumed silica which has been surface treated with a silazane.

Optionally, the compositions of the present invention further include at least one ultraviolet absorbing compound which is capable of absorbing significant amounts of ultraviolet radiation having wavelengths from about 200 nm to about 405 nm. Preferably, the ultraviolet absorbing compound is capable of copolymerizing with the organohydrosiloxane crosslinking reagent and the vinyl terminated polyorganosiloxane base resin. This capability allows the ultraviolet absorbing compound to covalently bind with the elastomer and precludes its mass transfer from the cured composition.

The high refractive index compositions of the present invention can be cured to polyorganosiloxane elastomers using conventional platinum cure techniques. Preferably, suitable silicone elastomer molding techniques are utilized to form molded objects, such as foldable, high refractive index intraocular lenses. The resulting molded elastomer maintains the highly superior optical clarity present in the uncured composition, and furthermore exhibits superior folding recovery. These important characteristics are attributed in part to the bimodal molecular weight ranges of the polyorganosiloxanes which cure to form strong interconnecting polymer networks and in part to the correlation between the optical resolution recovery of the folded intraocular lenses and the contents of fumed silica in the polyorganosiloxane compositions of the present invention. Intraocular lenses thus fabricated have smaller profiles after having been folded and maintain high optical resolution after unfolding, making them particularly useful in small incision intraocular lens implant surgery.

Further objectives, features and advantages of the curable, high refractive index polyorganosiloxane compositions of the present invention, as well as a better understanding thereof, will be afforded to those skilled in the art from a consideration of the following detailed explanation of preferred exemplary embodiments.

DETAILED DESCRIPTION OF EXEMPLARY EMBODIMENTS

The present invention provides high refractive index, curable polyorganosiloxane compositions which cure to polyorganosiloxane elastomers having superior optical clarity, highly improved optical resolution, and near 100% post-folding optical resolution recovery.

Because the compositions of the present invention are elastomeric and have refractive indices on the order of 1.46, they are useful for fabricating thin profile optical lenses which advantageously can be folded or rolled to a small profile. In particular, the combination of high refractive index and superior post-folding optical resolution recovery make the curable organosiloxane compositions of the present invention particularly suitable for the fabrication of intraocular lenses used in small incision implant procedures. However, the utility of the compositions of the present invention is not limited to intraocular lenses, but includes applications in which the combination of physical and optical characteristics of the cured polyorganosiloxane compositions are desirable. Accordingly, it is contemplated to be within the scope of the present invention to additionally provide compositions for corneal contact lenses and intrastromal lenses.

In a broad aspect, the present invention provides curable silica filled polyorganosiloxane compositions of at least two vinyl terminated copolymers of dimethylsiloxane and diphenylsiloxane. The polyorganosiloxane compositions have a multimodal molecular weight distribution with at least one vinyl terminated copolymer differing substantially in molecular weight from a second vinyl terminated copolymer. Once cured with a platinum or platinum containing catalyst and crosslinking reagent, the compositions of the present invention form mechanically strong and optically superior interconnecting polymer networks.

More particularly, the curable polyorganosiloxane compositions of the present invention include a base resin of at least two vinyl terminated copolymers of from about 80 mole % to about 95 mole % dimethylsiloxane and from about 5 mole % to about 20 mole % diphenylsiloxane. At least one first vinyl terminated copolymer is present in the composition at a concentration of from about 30 wt. % to about 55 wt. %, preferably about 42 wt. % to about 48 wt. %, and a molecular weight sufficient to provide the first vinyl terminated copolymer with a viscosity of from about 400 cps to about 2500 cps. Similarly, at least one second vinyl terminated copolymer of dimethylsiloxane and diphenylsiloxane is present at a concentration of from about 45 wt. % to about 70 wt. % and a molecular weight sufficient to provide a second vinyl terminated copolymer with a viscosity of from about 2500 cps to about 9500 cps. The exemplary polyorganosiloxane copolymer compositions further include filler material, catalyst, and organohydropolysiloxane crosslinking reagent.

The vinyl terminated copolymers of dimethylsiloxane and diphenylsiloxane utilized in the compositions of the present invention have the following general formula:

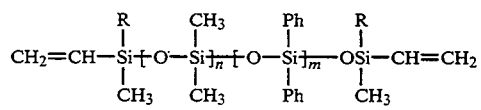

where R is a monovalent organic radical selected from the group consisting of $CH_3$ and $CH=CH_2$. Note that the vinyl terminated copolymers can include more than one terminal vinyl functionality. Preferred copolymers are random copolymers of dimethylsiloxane and diphenylsiloxane. However, block copolymers and alternating copolymers containing dimethylsiloxane and diphenylsiloxane in a regular repeating pattern are also contemplated as being within the scope of the present invention.

The values n and m indicate the number of dimethylsiloxane units and the number of diphenylsiloxane units, respectively, in the polyorganosiloxane copolymers. The at least one first vinyl terminated copolymer has a value of n+m sufficient to provide a first vinyl terminated copolymer viscosity of from about 400 cps to about 2500 cps and preferably from about 400 cps to about 1000 cps. Similarly, the at least one second vinyl terminated copolymer has a value of n+m sufficient to provide a second vinyl terminated copolymer viscosity of from about 2500 cps to about 9500 cps and preferably from about 4400 cps to about 5400 cps. Accordingly, exemplary embodiments of the present invention include first and second vinyl terminated copolymers having values of n from about 60 to about 200 and from about 200 to about 330, respectively. Similarly, these exemplary embodiments include first and second vinyl terminated copolymers having values of m from about 9 to about 35 and from about 35 to 55, respectively. Preferred exemplary embodiments have second vinyl terminated copolymer viscosities ranging from 4000 cps to 9500 cps and have values of n and m ranging from 225 to about 330 and 40 to 55, respectively. Moreover, while exemplary embodiments of the present invention include base resins of vinyl or divinyl terminated copolymers having from 5 mole % to 20 mole % diphenylsiloxane, preferred embodiments include vinyl or divinyl terminated copolymers having from 12 mole % to 18 mole % diphenylsiloxane. Most preferred embodiments have about 13-15 mole % diphenylsiloxane.

It is evident from the discussion above that the values n and m determine the molecular weight and viscosity of the first and second vinyl terminated copolymers. It is also apparent that the molecular weight distribution of the preferred polyorganosiloxane compositions of the present invention is bimodal. That is, the first and second vinyl terminated copolymers have distinguishably different molecular weights with little or no overlap. As will be discussed further below, this bimodal molecular weight distribution is believed to be responsible for the superior strength and excellent post-folding recovery characteristics of the highly interconnected network of polymer chains in the final cured organosiloxane polymer.

The filler material utilized in the polyorganosiloxane compositions of the present invention is preferably fumed silica having an average particle size on the order of less than about 11 nanometers. In order to obtain superior optical characteristics the particle size should be as small as possible. Fumed silica having an average particle size of about 7 nanometers in diameter is particularly suitable because the small particle size does not interfere with the wavelength of visible light and contributes to an improved optical resolution in the cured composition. Exemplary embodiments include fumed silica at concentrations ranging from 8 phr (parts per hundred parts resin) to 25 phr and preferably from 11 phr to 14 phr. Commercial fumed silica with particle sizes as low as 7 nm are available from a number of sources including Cabot and Sigma.

The most preferred exemplary embodiments of the present invention include from about 11 phr to 14 phr small particle size fumed silica which has been surface treated with a silazane. These silazane treated surfaces provide the fumed silica particles with a siloxane compatible surface. This characteristic improves the siloxane wettability of the fumed silica and further contributes to the superior optical qualities of the polyorganosiloxane compositions.

Preferred silazanes and methods for carrying out the fumed silica surface treatment include the in situ reaction of small particle size fumed silica with hexamethyldisilazane and/or 1,3-divinyltetramethyldisilazane. These silazanes readily react with the —OH functionalities on fumed silica, forming a trimethylsiloxane coating on the silica surface. The 1,3-divinyltetramethyldisilazane provides the added advantage of incorporating vinyl functionalities on the fumed silica surface which can covalently interact with the polyorganosiloxane copolymers during the curing process.

Crosslinking reagents suitable for use in the compositions of the present invention include organohydrosiloxanes having multiple active hydride functionalities for reacting with vinyl functionalities in a platinum cure system. One particularly suitable organohydrosiloxane is tetrakis(dimethylsiloxy)silane, which has four reactive hydride units per molecule. The organohydropolysiloxane is available from a variety of commercial sources including Petrarch. Advantageously, this organohydrosiloxane, which has a $SiO_2$ structure unit which makes it optically compatible with the vinyl terminated polyorganosiloxanes making up the base resin, also has a refractive index of about 1.46. This crosslinking reagent has the capability of reacting with up to four different copolymer chains during the curing process, resulting in a tightly crosslinked interconnecting polymeric network.

Additional suitable organohydrosiloxanes include random terpolymers of dimethylsiloxane, diphenylsiloxane, and methylhydrosiloxane. Organohydrosiloxanes containing combinations of these three siloxanes and having a refractive index close to 1.46 can be prepared using standard polysiloxane preparation techniques. A typical organohydropolysiloxane having utility as a crosslinking reagent in the compositions of the present invention has the following general structure:

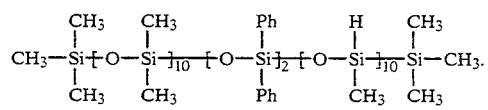

The relative amounts of dimethylsiloxane, diphenylsiloxane and methylhydrosiloxane in the above described terpolymer advantageously provide the crosslinking reagent with numerous active hydride functionalities and a refractive index which promotes superior optical clarity in the cured composition.

Optionally, the polyorganosiloxane copolymer compositions of the present invention further include an ultraviolet (UV) absorbing compound which preferably has a high absorptivity of ultraviolet radiation for wavelengths up to about 405 nm. When incorporated in organosiloxane compositions used to fabricate optical materials utilized in ophthalmic applications, these UV absorbing compounds are a safeguard against excessive UV radiation exposure to the retina and other ocular structures. Exemplary embodiments have from about 0.1 phr to as high as 10 phr UV absorbing compound and preferably from about 0.1 phr to about 2 phr. The preferred concentration of UV absorbing compound depends upon the molar absorptivity of the UV absorbing compound, with the more highly absorbing compounds being present at lower concentrations. Suitable UV absorbing compounds are those compounds having desirable absorption characteristics, minimum ocular toxicity and preferably having a sufficiently high solubility in the vinyl terminated organosiloxane copolymers. For example, any of a large variety of hydroxy benzophenones and hydroxyphenylbenzotriazoles, available from numerous commercial sources, have these physical and chemical characteristics.

In order to assure that no amount or negligible amounts of the UV absorbing compound is available to migrate to the surface of an ophthalmic lens once it is situated in the ocular environment, the UV absorbing compound preferably is capable of copolymerizing with the vinyl terminated organosiloxane copolymers utilized in the compositions of the present invention. Thus, for example, UV absorbing compounds having active vinyl functionalities and/or active silicone hydride functionalities are particularly suitable for incorporating into the vinyl terminated organosiloxane copolymers of the present invention. For example, vinyl/and or silicone hydride modified hydroxy benzophenones or hydroxy phenylbenzotriazoles incorporated in vinyl terminated organosiloxane copolymers will react with the vinyl terminated organosiloxane copolymers once a crosslinking reaction is initiated by platinum or platinum containing catalyst. More specifically, the allyloxypropyl modified hydroxy phenylbenzotriazole known as Tinuvin 326 or 2-[5-chloro-2H-benzotriazol-2-yl]-6-[1,1-dimethylethyl]-4-[2-propenyloxypropyl]phenol is particularly suitable because of its high absorptivity at wavelengths up to 405 nm, its solubility and its vinyl functionality.

It is also contemplated as being within the scope of the present invention to provide compositions which incorporate multi-functional UV absorber compounds. In particular, UV absorbing compounds having a plurality of silicone hydride functionalities have advantageous chemical reactivity properties. Multi-functional silicone hydride UV absorbers contribute to increased crosslinking and thus result in a "tighter" interconnecting polymer network in the final cured composition. Additionally, UV absorbing compounds are bulky and somewhat sterically hindered. By providing a plurality of reactive groups on the UV absorbing compound, there is a greater probability of forming covalent bonds with the polymerizing organosiloxane copolymers. If monofunctional UV absorbers are merely mixed with a curable silicone formulation, some of the UV absorber will incorporate into the silicone network. However, a substantial amount will remain unreacted and is available for extraction or migration to the surface of a formed intraocular lens within the ocular environment. Moreover, the multi-functional nature of the UV absorbing compound does not cause undesirable "chain termination" during the curing process which results in shortened polyorganosiloxane polymer chains and a reduced interconnecting network.

Exemplary multi-functional UV absorbers can be prepared by reacting any of the vinyl modified hydroxy benzophenones or -vinyl modified hydroxy phenylbenzotriazoles mentioned above with multi-functional active silicone hydrides. For example, when 2-[5-chloro-2H-benzotriazol-2yl-]-6-[1,1,-dimethylethyl]-4-[2-propenyloxypropyl]phenol is reacted with tetrakis(-dimethylsiloxy) silane, the resulting silicone hydride modified hydroxyphenylbenzotriazole has three reactive silicone hydride functionalities and can act as additional crosslinking reagent for the vinyl terminated organosiloxane copolymers. Similarly, this same hydroxy benzotriazole can be reacted with a terpolymer of dimethylsiloxane, diphenylsiloxane, and methylhydrosiloxane to form a UV absorbing compound having multiple hydride functionalities.

Preferred exemplary embodiments of the present invention further include small amounts of inhibitor, on the order of about 0.1 pmr (parts per million parts resin) to about 25 pmr, to extend the pot-life up to 8 hours. A wide variety of suitable inhibitors are commercially available and can be utilized in the compositions of the present invention. Specifically, 1,3,5,7- tetravinyltetramethyl-cyclotetrasiloxane and/or 1-octyn-3-ol provide sufficient inhibiting properties for incorporating in the compositions of the present invention.

The compositions of the present invention can be effectively cured to a crosslinked, high refractive index elastomeric material with interconnected polymer networks having superior optical properties. The cure reaction is preferably catalyzed with a platinum or platinum containing catalyst which is present at catalytic effective concentrations. Typical catalytic effective concentrations are from about 5 pmr to about 50 pmr. In addition to platinum, suitable platinum containing compounds having utility as catalysts in the compositions of the present invention include $H_2PtCl_6$, platinum-divinyltetramethyldisiloxane complex, and platinum-cycloyvinylmethyltetrasiloxane complex.

The preferred vinyl terminated organosiloxane copolymers, crosslinking reagent, fumed silica, UV absorber, inhibitor, and catalyst containing compositions of the present invention are homogeneous blends which cure to a high refractive index, elastomeric polyorganosiloxane. The compositions are prepared utilizing polymer and prepolymer formulating and mixing techniques known in the polymer art. Typically, these techniques include accurately weighing and/or accurately measuring volumes of the desired vinyl terminated organosiloxane copolymers, fumed silica, and additives and then transferring each component to suitable mixing equipment. Then the composition is mixed until a homogeneous blend of the components, which is ready for curing into the desired shaped article, is obtained.

In order to prepare lenses fabricated from the compositions of the present invention for ophthalmic applications, the preferred procedure is to provide lens molds of the desired shape and to then fill the molds with the above described uncured vinyl terminated organosiloxane compositions. The filled molds are then heated to a curing temperature and for a length of time sufficient to form a crosslinked interconnected polymer network. Typical curing temperatures and curing periods include from about 90° C. to about 160° C. and from about 1 min. to about 60 min.

Preferably, after curing the organosiloxane copolymers and forming the article or lens, the lens is extracted with a low molecular weight alcohol, such as ethyl alcohol or isopropyl alcohol. This step causes very low molecular weight and alcohol soluble organosiloxanes to be extracted from the lens and further provides a precautionary measure against their extraction in the ocular environment after the lens is in use. There is no detectable UV absorbing compound to be extracted because any UV absorbing agent has been covalently bound to the crosslinker.

Because the refractive index of the vinyl terminated organosiloxanes, fumed silica, and UV absorbers are very similar, each about 1.46, the resulting cured elastomers have superior optical clarity. Moreover, the multifunctional crosslinking reagents and/or UV absorbing compounds contribute to a highly crosslinked interconnecting network which is believed to be responsible for the 100% post-folding recovery exhibited by the cured compositions of the present invention. This property is further enhanced by the bimodal molecular weight distribution of the vinyl terminated organosiloxane copolymers which form interconnecting long and short polymer chains. The combined effect of the bimodal network and the tightly crosslinked network is a superior "memory" characteristic in the cured elastomer. This "memory" characteristic is exemplified by the cured elastomer's ability to recover its original dimensions and its optical resolution after deformation.

The exceptional optical and physical characteristics of the cured compositions of the present invention as well as exemplary compositions and procedures for their preparation are further illustrated by the following non-limiting examples.

EXAMPLE 1

Procedure for Preparing Terpolymer Crosslinking Reagent

A terpolymer of dimethylsiloxane, diphenylsiloxane, and methylhydrosiloxane was prepared by first combining 81 grams of hexamethyldisiloxane, 323 grams of octamethylcyclotetrasiloxane and a catalytic amount of triflic acid and allowing the reactants to polymerize at 60° C. for 16 hours. This reaction resulted in a yield of 354 grams of a 10 cps polydimethylsiloxane having trimethylsilyl end groups which was then allowed to equilibrate with 180 grams of octaphenylcyclotetrasiloxane in the presence of potassium silanoate catalyst at 140°-150° C. for 48 hours. This equilibration procedure resulted in a copolymer of dimethylsiloxane and diphenylsiloxane with a viscosity of 60 cps and a refractive index of 1.465. Then 468 grams of this copolymer was reacted with 172 grams of 1,3,5,7-tetrahydrotetramethylcyclotetrasiloxane in the presence of triflic acid catalyst at 50° C. for 3 days to provide a terpolymer having 10 dimethylsiloxane units, 2 diphenylsiloxane units, and 10 hydroxymethylsiloxane units.

EXAMPLE 2

Cured Organosiloxane with UV Absorber

A curable, high refractive index polyorganosiloxane composition was obtained by first preparing a base resin of 58 parts vinyl terminated dimethyldiphenylsiloxane having a viscosity of 2,500 cps and 42 parts vinyl terminated dimethyldiphenylsiloxane having a viscosity of 4,900 cps. Then 12 phr (parts per hundred parts resin) of fumed silica, 25 pmr (parts per million parts resin) of 1,3,5,7-tetravinyltetramethylcyclotetrasiloxane, an inhibitor, 0.5 phr of Tinuvin 326, an UV absorber, 15 pmr platinum catalyst and 5 phr of the terpolymer prepared in Example 1 were mixed with the base resin to form a homogeneous mixture. The mixture was poured into molds and slabs having dimensions of 3 inch×4 inch were prepared, cured at 130°-140° C. for 45-60 minutes, and post-cured at 110° C. for 16 hours.

Intraocular lenses were similarly molded and extracted in ethanol for 24 hours at 25° C. Following this extraction step a variety of physical tests were performed on the slabs including weight loss after extraction, tensile strength, elongation at break, and Shore hardness. The intraocular lenses were tested for optical resolution and folding recovery at both low and high diopters resolution. The wavelength at which the ultraviolet cut-off occurs was also determined. Table I illustrates the results of these tests.

TABLE I

| | |
|---|---|
| Weight Loss after extraction | <4.5 wt % |
| Tensile strength | 400 psi |
| Elongation at Break | 350% |
| Shore Hardness | 29 |
| Optical efficiency post folding (30 diopter lens) | |
| in air | 64% |
| in aqueous | 85% |
| Optical efficiency post folding (15 diopter lens) | |
| in air | 90% |
| in aqueous | 90% |
| Ultraviolet cut-off | 400 nm |

EXAMPLE 3

Cured Organosiloxane without UV Absorbing Compound

A curable high refractive index organosiloxane composition was obtained by first preparing a base resin of 58 parts vinyl terminated dimethyldiphenylsiloxane having a viscosity of 400 cps and 42 parts vinyl terminated dimethyldiphenylsiloxane having a viscosity of 9,500 cps. Then 12 phr of fumed silica, 25 pmr of 1,3,5,7-tetravinyltetramethylcyclotetrasiloxane, 2.35 phr of tetrakis(dimethylsiloxy) silane and 15 pmr of platinum catalyst were mixed with the base resin to form a homogeneous mixture. The mixture was poured into molds and slabs having dimensions of 3 inch×4 inch were prepared, cured at 130°-140° C. for 45-60 minutes, and post-cured at 110° C. for 16 hours.

Intraocular lenses were similarly molded and extracted in ethanol for 24 hours at 25° C. Following this extraction step a variety of physical tests were performed on the slabs including weight loss after extraction, tensile strength, elongation at break, and Shore hardness. The intraocular lenses were tested for optical resolution and folding recovery at both low and high diopters resolution. The wavelength at which the ultraviolet cut-off occurs was also determined. The results obtained from these tests for samples not containing UV absorbing compound were similar to those reported in Table I above for samples containing UV absorbing compound.

EXAMPLE 4

Preparation of UV Absorbing Compound with Multiple Hydrides

In order to prepare a UV absorbing compound having a plurality of silicone hydride functionalities, a mixture of 14.7 grams of the vinyl modified hydroxy benzotriazole, (2-[5-chloro-2H-benzotriazol-2-yl]-6-[1,1-dimethylethyl]-4-[2-propenyloxypropyl]phenol), 100 grams of tetrakis(dimethylsiloxy) silane, and 2 µl of platinum catalyst $H_2PtCl_6$, was stirred at 70° C.–80° C. for 48 hours under an inert gas atmosphere. The product obtained from this reaction was analyzed by $^1H$ NMR to determine the presence of vinyl protons which would indicate incomplete conversion of the vinyl functionalities to silicone hydride. The $^1H$ NMR results showed no detectable vinyl protons indicating complete hydrosilylation conversion to silicone hydride.

lists the various ingredients and illustrates the results of folding recovery and tensile strength tests.

TABLE II

| TEST # | Low MW vinyl terminated polyorganosiloxane (grams) | High MW vinyl terminated polyorganosiloxane (grams) | Crosslinking Reagent | Fumed Silica (grams) | Pre-Folding Optical Resolution (%) | Post-Folding Optical Resolution (%) | Tensile Strength (psi) |
|---|---|---|---|---|---|---|---|
| 1 | 42 | 58 | QXL* | 50 | 60 | <10 | 825 |
| 2 | **** | **** | QXL* | 20 | 71.6 | 35.8 | 695 |
| 3 | **** | **** | terpolymer** | 20 | 71.6 | 28.5 | 500 |
| 4 | 42 | 58 | QXL* | 20 | 71.6 | 64 | 750 |
| 5 | 42 | 58 | QXL* | 11 | 71.6 | 71.6 | 450 |
| 6 | 42 | 58 | QXL* | 8 | 71.6 | 71.6 | 279 |
| 7 | 42 | 58 | UV-QXL*** | 14 | 71.6 | 71.6 | 480 |
| 8 | 42 | 58 | UV-QXL*** | 13 | 71.6 | 71.6 | 480 |
| 9 | 42 | 58 | UV-QXL*** | 11 | 71.6 | 71.6 | 440 |

*tetrakis(dimethylsiloxy)silane
**diphenysiloxane, dimethylsiloxane and methylhydrosiloxane copolymer
***reaction product of 2-[5-chloro-2H-benzotriazol-2-yl]-6-[1,1-dimethylethyl]-4-[2-propenyloxypropyl]phenol and tetrakis(dimethyl- siloxy)silane
****momodal MW polyorganosiloxane It should be noted that the mixture containing the UV absorbing compound prepared above can be utilized both as the source of UV absorbing compound and as crosslinker for the copolymer reaction mixture. In the reaction described above, 14.7 grams (0.0368 mole) of the UV absorber was reacted with 100 grams (0.304 mole) of the crosslinker tetrakis(dimethylsiloxy) silane. There are 4 Si—H functional groups in each crosslinker while there is only one vinyl functional group in each UV absorber. Thus, the mole ratio of the crosslinker to the UV absorber is 8/1 and only one Si—H group out of 8 crosslinker molecules will react with one UV absorber molecule. The resulting mixture contains the crosslinker tetrakis-(dimethylsiloxy) silane and the UV-crosslinker which has three Si—H functional groups available for crosslinking a silicone network. The ratio of the crosslinker to UV absorber-crosslinker in the final mixture is about 7/1.

EXAMPLE 5

Cured Polyorganosiloxane Composition with UV Absorbing Compound

A curable, high refractive index polyorganosiloxane composition was obtained by first preparing a base resin of vinyl terminated dimethyldiphenylsiloxane having a viscosity of 4,900 cps and vinyl terminated dimethyldiphenylsiloxane having a viscosity of 700 cps. For comparison with the bimodal MW polyorganosiloxane composition a monomodal MW polyorganosiloxane having a viscosity of 4900 cps was tested. Then 12 phr of fumed silica, 25 mpr of 1,3,5,7-tetravinyltetramethylcyclotetrasiloxane inhibitor, 1.85 phr of Tinuvin 326 UV absorbing compound, and 15 pmr of platinum catalyst were mixed with the base resin to form a homogeneous mixture. The mixture was poured into molds and slabs having dimensions of 3 inch×4 inch were prepared, cured at 130°–140° C. for 45–60 minutes, and post-cured at 110° C. for 16 hours.

Intraocular lenses were similarly molded and extracted in ethanol for 24 hours at 25° C. Following this extraction step a variety of physical tests were performed on the slabs including tensile strength and tear strength. The 30 diopter intraocular lenses were tested for optical folding recovery and resolution. Table II It can be seen that the higher the percentage of fumed silica the lower the folding recovery of the optical resolution of the folded IOLs will be (see Tests #1–5). 100% folding recovery can be obtained with UV-QXL as the crosslinker when 11–14 parts of fumed silica was used (see Tests #7–9).

It can also be seen that formulations of higher filler percentages have higher tensile strength but lower folding recoveries. Apparently the fumed silica interacts with polysiloxane to enhance the mechanical properties and at the same time to reduce the elasticity of the polysiloxane. As a result, the optical folding recovery is completely lost when 50% of fumed silica is used. These two properties can be balanced in order to prepare IOLs with 100% folding recovery and sufficient mechanical strength.

It is also observed that IOLs made from polysiloxanes with bimodal distribution in molecular weights have better optical resolution recoveries than those with monomodal molecular weight distributions (see Tests #2–4).

EXAMPLE 6

Properties of IOLs Prepared from Organosiloxane Compositions of the Present Invention Compared with Commercial IOLs A curable high refractive index polyorganosiloxane composition was obtained by first preparing a base resin of 52 parts vinyl terminated dimethyldiphenylsiloxane having a viscosity of 5000 cps and 48 parts vinyl terminated dimethyldiphenylsiloxane having a viscosity of 700 cps. Then 13 phr of fumed silica, 25 pmr of 1,3,5,7-tetravinyltetrametkylcyclotetrasiloxane inhibitor, 2 phr of UV absorbing compound prepared as in Example 4, and 15 pmr of platinum catalyst was mixed with the base resin to form a homogeneous mixture. The mixture was injected into molds suitable for preparing intraocular lenses, cured at 110°–140° C. for 1–10 minutes, and post-cured at 110° C. for 2 hours.

The resulting IOLs were extracted in ethanol for 24 hours at 25° C. Following this extraction step a variety of physical and optical tests were performed on the IOLs. The same tests were also performed on two commercial silicone elastomer, foldable IOLs, identified as commercial A and commercial B. Table III illustrates the results of these tests.

TABLE III

| TEST | COMMERCIAL A | COMMERCIAL B | IOL OF PRESENT INVENTION |
|---|---|---|---|
| Curability | 10 min @ 130° C. | 10 min @ 130° C. | 10 min @ 130° C. |
| Refractive Index | 1.4130 ± 0.0005 | 1.4127 ± 0.0005 | 1.4629 ± 0.0005 |
| Weight Loss | 4.1% ± 0.1% | 5.2% ± 0.1% | 3.0% ± 0.1% |
| Overall Shrinkage | 4.5% ± 0.2% | 4.3% ± 0.2% | 3.0% ± 0.5% |
| Tensile Strength | 513 ± 40 [PSI] | 842 ± 70 [PSI] | 500 ± 50 [PSI] |
| Elongation | 484% ± 40% | 163% ± 10% | 495% ± 40% |
| Tear Resistance | 42 + 4 [PLI] | 16 + 2 [PLI] | 25 + 3 [PLI] |
| Pre-Folding Resolution Efficiency | 72% ± 7%[Lo Diop.]<br>64% ± 7%[Hi Diop.] | 72% ± 7%[Lo Diop.]<br>64% ± 7%[Hi Diop.] | >90%[Lo Diop.]<br>80%[Hi Diop] |
| Post-Folding Resolution Efficiency | 72% ± 7%[Lo Diop.]<br>64% ± 7%[Hi Diop.] | 72% ± 7%[Lo Diop.]<br>64% ± 7%[Hi Diop.] | >90%[Lo Diop.]<br>72% ± 7%[Hi Diop] |
| Folding Recovery | 100% | 100% | 100% |
| Auto-clavability | Yes | Yes | Yes |
| Durometer* | 31 ± 4 | 45 ± 3 | 29 ± 1 |
| Specific Gravity | 1.05 ± 0.02 | 1.07 ± 0.02 | 1.01 ± 0.02 |
| UV Cut-off | | | 400.2 nm @ 95% abs [2 mm thickness] |

*Lower durometer reading will cause the minimum "spring" effect during the lens unfolding process.

EXAMPLE 7

Polyorganosiloxane copolymers having utility in the curable high refractive index organosiloxane compositions of the present invention were prepared as follows:

A vinyl terminated end blocker was prepared by adding 2950 grams of octamethylcyclotetrasiloxane ($D_4$), purchased from Petrarch, 500 grams of 1,3-divinyltetramethyldisiloxane and 15 grams of tetramethylammonium hydroxide pentahydrate to a 5 L 3-neck round bottom flask equipped with a magnetic stirring bar, a reflux condenser, and a thermometer. The components were reacted at 80°–100° C. for 72 hours while stirring under constant positive argon atmosphere. The reacted mixture was allowed to cool and its viscosity was determined to be 15 cps.

The reacted mixture was worked-up by adding 250 mL of petroleum ether and 400 mL of water for every 1000 mL of mixture. Then the mixture was washed with dilute HCl (0.01N) aqueous solution in a 2 L separatory funnel until the pH of the washings was 6.0–6.5. Following the dilute acid wash, the mixture was washed with three separate portions of fresh water. The organic layer was drained into a crystallizing dish and dried in a vacuum oven at 60° C.

Vinyl terminated polyorganosiloxane copolymers were prepared by adding 768 grams of $D_4$, 336 grams of octaphenylcyclotetrasiloxane ($D_4^{Ph}$) and 48.6 grams of the end blocker prepared above to a 2 L round bottom flask equipped with a magnetic stirring bar, a reflux condenser and a thermometer. The mixture was heated to 140° C. in an oil bath and 0.2 grams of potassium silanoate was added while stirring under argon. The reaction was stirred for 3 days at 140° C. and at the end of the third day, the viscosity was measured to be 4900 cps at room temperature. On the fourth day no further viscosity changes were observed. After cooling to room temperature, the mixture was extracted with 10% tetrahydrofuran in ethanol 4 times, dried under vacuum and filtered through a Whatman ashless filter paper in a Gelman stainless steel filter under 90 psi.

A vinyl terminated polyorganosiloxane copolymer having a viscosity of 700 cps was prepared in a manner similar to that above except 654 grams of $D_4$, 319 grams of $D_4^{Ph}$, and 145.5 grams of end blocker were utilized in the reaction.

Having thus described exemplary embodiments of the present invention, it should be noted by those skilled in the art that the disclosures herein are exemplary only and that alternatives, adaptations and modifications may be made within the scope of the present invention.

We claim:

1. A high refractive index, curable polyorganosiloxane composition useful for fabricating intraocular lenses, said composition comprising:

about 30 wt. % to about 55 wt. % of a first vinyl terminated copolymer resin based on the total amount of the first and second vinyl terminated copolymer resins, said first vinyl terminated copolymer resin having about 80 mole % to about 95 mole % dimethylsiloxane and about 5 mole % to about 20 mole % diphenylsiloxane, said first vinyl terminated copolymer resin having a molecular weight sufficient to provide a first vinyl terminated copolymer resin viscosity of about 400 cps to about 2500 cps;

about 45 wt. % to about 70 wt. % of a second vinyl terminated copolymer resin based on the total amount of the first and second vinyl terminated copolymer resins, said second vinyl terminated copolymer resin having about 80 mole % to about 95 mole % dimethylsiloxane and about 5 mole % to about 20 mole % diphenylsiloxane, said second vinyl terminated copolymer resin having a molecular weight sufficient to provide a second vinyl terminated copolymer resin viscosity of about 2500 cps to about 9500 cps;

about 8 to about 25 parts of fumed silica filler per hundred parts resin;

tetrakis(dimethylsiloxy) silane crosslinking reagent; and

2-[5-chloro-2H-benzotriazol-2-yl]-6-[1,1-dimethylethyl]-4-[2-propenyloxypropyl]phenol hydrosilylated with tetrakis(dimethylsiloxy)silane.

2. The high refractive index, curable polyorganosiloxane composition of claim 1 wherein said first vinyl terminated copolymer resin has the formula:

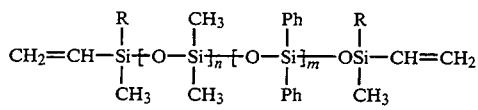

where R is a monovalent organic radical selected from the group consisting of $CH_3$ and $CH=CH_2$ and n+m is an integer sufficient to provide said first vinyl terminated copolymer viscosity of from about 400 cps to about 2500 cps.

3. The high refractive index, curable polyorganosiloxane composition of claim 1 wherein said second vinyl terminated copolymer resin has the formula:

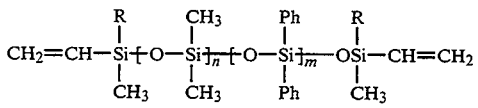

where R is a monovalent organic radical selected from the group consisting of $CH_3$ and $CH=CH_2$ and n+m is an integer sufficient to provide said second vinyl terminated copolymer viscosity of from about 2500 cps to about 9500 cps.

4. The high refractive index, curable polyorganosiloxane composition of claim 1 wherein said fumed silica filler has an average particle diameter of from about 7 nanometers to about 11 nanometers.

5. The high refractive index, curable polyorganosiloxane composition of claim 1 wherein said fumed silica is surface treated with a member selected from the group consisting of hexamethyldisilazane and 1,3-divinyltetramethyldisilazane.

6. An elastomeric, optically clear, high refractive index lens having superior post-folding optical resolution recovery, said lens comprising a polyorganosiloxane obtained by curing the curable, high refractive index, polyorganosiloxane composition of claim 1.

7. A high refractive index, curable polyorganosiloxane composition useful for fabricating intraocular lenses, said composition comprising:
about 30 wt. % to about 55 wt. % of a first vinyl terminated copolymer resin based on the total amount of the first and second vinyl terminated copolymer resins, said first vinyl terminated copolymer resin having about 80 mole % to about 95 mole % dimethylsiloxane and about 5 mole % to about 20 mole % diphenylsiloxane, said first vinyl terminated copolymer resin having a molecular weight sufficient to provide a first vinyl terminated copolymer resin viscosity of about 400 cps to about 2500 cps;
about 45 wt. % to about 70 wt. % of a second vinyl terminated copolymer resin based on the total amount of the first and second vinyl terminated copolymer resins, said second vinyl terminated copolymer resin having about 80 mole % to about 95 mole % dimethylsiloxane and about 5 mole % to about 20 mole % diphenylsiloxane, said second vinyl terminated copolymer resin having a molecular weight sufficient to provide a second vinyl terminated copolymer resin viscosity of about 2500 cps to about 9500 cps;
about 8 to about 25 parts of fumed silica filler per hundred parts resin;
tetrakis(dimethylsiloxy) silane crosslinking reagent; and
2-[5-chloro-2H-benzotriazol-2-yl]-6-[1,1-dimethylethyl]-4-[2-propenyloxypropyl]phenol hydrosilylated with a terpolymer of dimethylsiloxane, diphenylsiloxane, and methylhydrosiloxane.

8. The high refractive index, curable polyorganosiloxane composition of claim 7 wherein said fumed silica has an average particle size of about 7 nanometers to about 11 nanometers.

9. An elastomeric, optically clear, high refractive index lens having superior postfolding optical resolution recovery, said lens comprising a polyorganosiloxane obtained by curing the curable, high refractive index, polyorganosiloxane composition of claim 7.

10. The high refractive index, curable polyorganosiloxane composition of claim 7 wherein said fumed silica is surface treated with a member selected from the group consisting of hexamethyldisilazane and 1,3-divinyltetramethyldisilazane.

11. A high refractive index, curable polyorganosiloxane composition useful for fabricating intraocular lenses, said composition comprising:
about 42 wt. % to about 48 wt. % of a first vinyl terminated copolymer resin based on the total amount of the first and second vinyl terminated copolymer resins, said first vinyl terminated copolymer resin having about 82 mole % to about 88 mole % dimethylsiloxane and about 12 mole % to about 18 mole % diphenylsiloxane, said first vinyl terminated copolymer resin having a molecular weight sufficient to provide a first vinyl terminated copolymer resin viscosity of about 400 cps to about 1000 cps, and
about 52 wt. % to about 58 wt. % of a second vinyl terminated copolymer resin based on the total amount of the first and second vinyl terminated copolymer resins, said second vinyl terminated copolymer resin having about 82 mole % to about 88 mole % dimethylsiloxane and about 12 mole % to about 18 mole % diphenylsiloxane, said second vinyl terminated copolymer resin having a molecular weight sufficient to provide a second vinyl terminated copolymer resin viscosity of about 4400 cps to about 5400 cps;
about 8 to about 25 parts of fumed silica filler per hundred parts resin;
tetrakis(dimethylsiloxy) silane crosslinking reagent; and
2-[5-chloro-2H-benzotriazol-2-yl]-611,1-dimethylethyl]-4-[2-propenyloxypropyl]phenol hydrosilylated with tetrakis(dimethylsiloxy)silane.

12. An elastomeric, optically clear, high refractive index lens having superior postfolding optical resolution recovery, said lens comprising a polyorganosiloxane obtained by curing the curable, high refractive index, polyorganosiloxane composition of claim 11.

13. The high refractive index, curable polyorganosiloxane composition of claim 11 wherein said fumed silica filler has an average particle diameter of from about 7 nanometers to about 11 nanometers.

14. The high refractive index, curable polyorganosiloxane composition of claim 11 wherein said fumed silica is surface treated with a member selected from the group consisting of hexamethyldisilazane and 1,3-divinyltetramethyldisilazane.

15. A high refractive index, curable polyorganosiloxane composition useful for fabricating intraocular lenses, said composition comprising:
about 42 wt. % to about 48 wt. % of a first vinyl terminated copolymer resin based on the total amount of the first and second vinyl terminated copolymer resins, said first vinyl terminated copolymer resin having about 82 mole % to about 88 mole % dimethylsiloxane and about 12 mole % to about 18 mole % diphenylsiloxane, said first vinyl terminated copolymer resin having a molecular weight sufficient to provide a first vinyl terminated copolymer resin viscosity of about 400 cps to about 1000 cps, and
about 52 wt. % to about 58 wt. % of a second vinyl terminated copolymer resin based on the total amount of the first and second vinyl terminated copolymer resins, said second vinyl terminated copolymer resin having about 82 mole % to about 88 mole % dimethylsiloxane and about 12 mole % to about 18 mole % diphenylsiloxane, said second vinyl terminated copolymer resin having a molecular weight sufficient to provide a second vinyl terminated copolymer resin viscosity of about 4400 cps to about 5400 cps;
about 8 to about 25 parts of fumed silica filler per hundred parts resin;
tetrakis(dimethylsiloxy) silane crosslinking reagent; and
2-[5-chloro-2H-benzotriazol-2-yl]-6[1,1-dimethylethyl]-4-[2-propenyloxypropyl]phenol hydrosilylated with a terpolymer of dimethylsiloxane, diphenylsiloxane, and methylhydrosiloxane.

16. An elastomeric, optically clear, high refractive index lens having superior postfolding optical resolution recovery, said lens comprising a polyorganosiloxane obtained by curing the curable, high refractive index, polyorganosiloxane composition of claim 15.

17. The high refractive index, curable polyorganosiloxane composition of claim 15 wherein said fumed silica filler has an average particle diameter of from about 7 nanometers to about 11 nanometers.

18. The high refractive index, curable polyorganosiloxane composition of claim 15 wherein said fumed silica is surface treated with a member selected from the group consisting of hexamethyldisilazane and 1,3-divinyltetramethyldisilazane.

19. A high refractive index, curable polyorganosiloxane composition useful for fabricating intraocular lenses, said composition consisting essentially of:
about 42 wt. % to about 48 wt. % of a first vinyl terminated copolymer resin based on the total amount of the first and second vinyl terminated copolymer resins, said first vinyl terminated copolymer resin having about 82 mole % to about 88 mole % dimethylsiloxane and about 12 mole % to about 18 mole % diphenylsiloxane, said first vinyl terminated copolymer resin having a molecular weight sufficient to provide a first vinyl terminated copolymer resin viscosity of about 400 cps to about 1000 cps, and
about 52 wt. % to about 58 wt. % of a second vinyl terminated copolymer resin based on the total amount of the first and second vinyl terminated copolymer resins, said second vinyl terminated copolymer resin having about 82 mole % to about 88 mole % dimethylsiloxane and about 12 mole % to about 18 mole % diphenylsiloxane, said second vinyl terminated copolymer resin having a molecular weight sufficient to provide a second vinyl terminated copolymer resin viscosity of about 4400 cps to about 5400 cps;
about 11 to about 14 parts of fumed silica filler per hundred parts resin;
about 5 to about 50 parts of platinum containing catalyst per million parts resin;
about 1.5 to about 5 parts of tetrakis(dimethylsiloxy) silane crosslinking reagent per hundred parts resin; and
about 0.1 to about 2 parts of 2-[5-chloro-2H-benzotriazol-2-yl]-6-[1,1-dimethylethyl]-4-[2-propenyloxypropyl]phenol ultraviolet absorbing compound hydrosilylated with tetrakis(dimethylsiloxy) silane.

20. An elastomeric, optically clear, high refractive index lens having superior postfolding optical resolution recovery, said lens comprising a polyorganosiloxane obtained
by curing the curable, high refractive index, polyorganosiloxane composition of claim 19.

21. A high refractive index, curable polyorganosiloxane composition useful for fabricating intraocular lenses, said composition consisting essentially of:
about 42 wt. % to about 48 wt. % of a first vinyl terminated copolymer resin based on the total amount of the first and second vinyl terminated copolymer resins, said first vinyl terminated copolymer resin having about 82 mole % to about 88 mole % dimethylsiloxane and about 12 mole % to about 18 mole % diphenylsiloxane, said first vinyl terminated copolymer resin having a molecular weight sufficient to provide a first vinyl terminated copolymer resin viscosity of about 400 cps to about 1000 cps, and
about 52 wt. % to about 58 wt. % of a second vinyl terminated copolymer resin based on the total amount of the first and second vinyl terminated copolymer resins, said second vinyl terminated copolymer resin having about 82 mole % to about 88 mole % dimethylsiloxane and about 12 mole % to about 18 mole % diphenylsiloxane, said second vinyl terminated copolymer resin having a molecular weight sufficient to provide a second vinyl terminated copolymer resin viscosity of about 4400 cps to about 5400 cps;
about 11 to about 14 parts of fumed silica filler per hundred parts resin;
about 5 to about 50 parts of platinum containing catalyst per million parts resin;
about 1.5 to about 5 parts of tetrakis(dimethylsiloxy)-silane crosslinking reagent per hundred parts resin; and
about 0.1 to about 2 parts of 2-[5-chloro-2H-benzotriazol-2-yl]-6-[1,1-dimethylethyl]-4-[2-propenyloxypropyl]phenol ultraviolet absorbing compound hydrosilylated with a terpolymer of dimethylsiloxane, diphenylsiloxane, and methylhydrosiloxane.

22. An elastomeric, optically clear, high refractive index lens having superior postfolding optical resolution recovery, said lens comprising a polyorganosiloxane obtained by curing the curable, high refractive index, polyorganosiloxane composition of claim 21.

* * * * *